United States Patent [19]

Silks, III et al.

[11] Patent Number: 5,122,472
[45] Date of Patent: Jun. 16, 1992

[54] CHALCOGEN-BASED CHIRAL REAGENTS AND METHOD FOR NUCLEAR MAGNETIC RESONANCE DETECTION OF STEREOCHEMICAL ASSIGNMENTS AND ENANTIOMERIC RATIOS

[75] Inventors: Louis A. Silks, III; R. Bruce Dunlap, both of Columbia; Jerome D. Odom, Ridgeway, all of S.C.

[73] Assignee: University of South Carolina, Columbia, S.C.

[21] Appl. No.: 418,129

[22] Filed: Oct. 6, 1989

[51] Int. Cl.$^5$ .......................................... C07D 263/16
[52] U.S. Cl. ................................... 436/173; 548/229; 548/230; 562/899
[58] Field of Search .............. 548/229, 230; 436/173; 562/899

[56] References Cited

U.S. PATENT DOCUMENTS

| | | | |
|---|---|---|---|
| 2,525,200 | 10/1950 | Bergmann | 548/229 |
| 3,221,021 | 11/1965 | Hickner | 548/229 |
| 3,716,335 | 2/1973 | Ullmann | 436/173 |
| 3,898,276 | 8/1975 | Otto | 562/899 |
| 3,947,465 | 3/1976 | Coll | 548/229 |
| 3,966,409 | 6/1976 | Hrvoic | 436/173 |
| 4,099,918 | 7/1978 | Keana | 436/123 |
| 4,945,234 | 7/1990 | Goodman et al. | 436/173 |

OTHER PUBLICATIONS

Michelsen et al., Chem. Abstr., vol. 103 entry 104643y (1985).
Liota et al., Chem. Abstr., vol. 103 entry 104644z (1985).
Dean et al., Chem. Abst., vol. 106 entry 206683r (1987).
Michelsen et al., Chem. Scr., vol. 24, 8251-2 (1984).
Tomta Chem. Abstract 112:118487 destracting JP 01,224,358.
Kjer, et al., Heterocycles (1989) vol. 28 pp. 269–273.
Mullin, et al., Biochemistry 1986, vol. 25, pp. 5625-5632.
Pirkle and Hanover, NMR Chiral Solvating Agents pp. 286–299.
Cullen, et al., J. Am. Chem. Soc. 1981, 103, pp. 7055-7057.
Poleschner, et al., Organic Magnetic Resonance, 1984, 22, pp. 480–485 and pp. 1206–1208.
Wong, J. Magnetic Resonance, 1984, 57, pp. 463–470.

(List continued on next page.)

*Primary Examiner*—Donald G. Daus
*Attorney, Agent, or Firm*—Brumbaugh, Graves, Donohue & Raymond

[57] ABSTRACT

Selenium reagents when coupled to a compound containing an asymmetric carbon atom can be used in a highly sensitive method for determination of enantiomeric purity and for stereochemical assignment. Preferred reagents include a selenocarbonyl moiety (Se=C) and a reactive center for coupling to the compound of interest. Particularly preferred selenocarbonyls for use in the invention are selenooxazolidinones of the formula

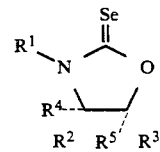

wherein $R^2$, $R^3$, $R^4$ and $R^5$ are selected from among hydrogen, alkyl of up to 10 carbons and aryl having up to 12 carbon atoms in the ring system. The substituent $R^1$ is selected to facilitate the formation of a bond between the nitrogen atom of the selenooxazolidinone reagent and the compound of interest. Since the ability of the reagent to resolve enantiomers decreases as the number of bonds between the selenium and the asymmetric carbon increases, the reactive center is preferably located no more than three bonds from the selenium atom.

7 Claims, 1 Drawing Sheet

OTHER PUBLICATIONS

Luthra, et al., J. Organic Metallic Chemistry (1988) vol. 354, pp. 51–62.
Parker, et al., J. Chem. Soc. Perkin Trans. (1983) pp. 83–88.
Shapiro, et al., J. Org. Chem. (1989) 54, pp. 5826–5828.
Pirkle, et al., Tetrahedron Ltrs. (1985) vol. 26, pp. 2989–2992.
Schwab, et al., J. Am. Chem. Soc. (1983), vol. 105, pp. 4800–4808.
Schwab, et al., J. Am. Chem. Soc. (1989), vol. 111, pp. 1057–1063.
Gerlach, et al., J. C. S. Chem. Comm. (1973) pp. 274–275.
Mullen, et al., J. Am. Chem. Soc. (1985) vol. 107, pp. 7187–7189.
Luthra, et al., Analytical Biochemistry (1981) vol. 117, pp. 94–102.
Odom, Selenium Biochemistry Chemical and Physical Studies (1983) pp. 1–16.
Dowd, et al., Mag. Res. Chem. (1988) vol. 26, pp. 1–3.
Odom, et al., J. Am. Chem. Soc. (1979) vol. 101 pp. 5815–5822.
Gombler, Phosphorus and Sulfur, (1988) vol. 38, pp. 231–243.
Boccanfuso, et al., Bioorganic Chemistry (1989) vol. 17, pp. 231–239.
Laitinen, et al., Inorg. Chem. (1987) vol. 26 pp. 2598–2603.
Luthra, et al., J. Mag. Res. (1982) vol. 46, pp. 152–157.
Luthra, et al., J. Mag. Res. (1983) vol. 52, pp. 318–322.
Luthra, et al., J. Biological Chemistry (1982) vol. 257, pp. 1142–1144.
Krief, et al., Tetrahedron (1989) 45 pp. 2005–2022.
Reich, et al., J. Am. Chem. Soc. (1987) 109 pp. 5549–5551.
Francotte, et al., Helvetica Chimica Acta (1987) 70 pp. 1569–1582.
Dale, et al., J. Am. Chem. Soc. (1973) pp. 512–519.
Williams, et al., J. Am. Chem. (1988) vol. 110, pp. 1547–1557.
Vandewalle et al., Tetrahedron (1986) vol. 42, pp. 4035–4043.
Trost, et al., J. Am. Chem. Soc. (1989) vol. 111 pp. 7487–7500.
Rabenstein, et al., Mag. Res. Chem. (1988) vol. 26, pp. 1079–1085.
Weiss, et al., J. Mag. Res. (1983) vol. 55 pp. 397–407.
Dunlap, Phosphorus and Sulfur (1988) vol. 38, pp. 217–229.
Luthra, in the Chemistry of Organic Selenium and Tellurium Compounds New York, Wiley (1986) vol. 1, pp. 189–241.
Johnson, J. Am. Chem. Soc. (1984) vol. 106 pp. 5019–5020.
Feringa, J. Am. Chem. Soc. (1985) vol. 107, pp. 4798–4799.
Aldrich Chemical Co. Catalog, pp. 872–873.

CHALCOGEN-BASED CHIRAL REAGENTS AND METHOD FOR NUCLEAR MAGNETIC RESONANCE DETECTION OF STEREOCHEMICAL ASSIGNMENTS AND ENANTIOMERIC RATIOS

BACKGROUND OF THE INVENTION

This application relates to a method and reagents for using $^{77}$Se-Nuclear magnetic resonance spectroscopy to provide stereochemical assignments and to evaluate the enantiomeric purity of a composition. The application further relates to a synthetic method for preparing the reagents.

Obtaining compositions of high or at least well defined optical purity is of importance in a great many practical applications of synthetic organic chemistry. Many pharmaceuticals are most active in one enantiomeric form. Similarly, different enantiomers can have very distinctive organoleptic properties making the question of enantiomeric purity of significance in the flavoring and fragrancing arts. On a more academic level, evaluation of enantiomeric products can provide valuable insights into both conventional and enzymatic reaction mechanisms.

Over the past decade considerable effort has been spent in numerous laboratories developing new synthetic methodology in the quest for improved asymmetric synthesis. This goal has been attained in many instances through the exertion of stereochemical control to achieve optical purity. The challenge to conceive and execute a new strategy which provides the organic chemist with either optically pure starting materials or an enantiospecific total synthesis of an important natural product is paramount. While innovation is giving the synthetic chemist an arsenal of methods for asymmetric synthesis, a continuing problem has been the facile determination of enantiomeric or diastereomeric purity in natural or synthetically constructed molecules.

Typically, if the optical purity cannot be directly evaluated using physical methods, the organic chemist alters the molecule, frequently in a multistep manner, to a derivative whose rotation is a reported literature value. This method, although tedious and time consuming, gives reliable and consistent results if the following caveats are recognized: 1. The solvent must be the same as the one in which the rotation was originally reported (e.g., verbenol, a natural product, is levorotatory in chloroform and dextrorotatory in acetone or in methanol); 2. Trace impurities can cause errors in polarimetric determinations; and 3. Reported $[\alpha]D$ values are not uniformly accurate, e.g., exo-brevicomin reportedly has rotations of (in ether) +69,30, −69,70, and +72.40, −73.60. Clearly, the data obtained from optical rotations must include the exact conditions in which the determinations were made.

For some types of compounds, chromatographic methods have been suitable for the determination of the enantiomeric purity. Francotte et al., Helv. Chim. Acta. 70:1569 (1970). Separation is possible by using a chiral stationary phase or by converting the enantiomers into diastereomers, followed by chromatographic fractionation on an achiral stationary phase. In some cases this method has been excellent results but, it basically remains a trial and error procedure.

An an alternative to optical and chromatographic approaches, techniques have been developed to determine the ratios of enantiomers using nuclear magnetic resonance spectroscopy (NMR). One such method involves the use of chiral europium shift reagents (e.g., Eu(tfc)$_3$ or Eu(hfc)$_3$) for NMR detection of ratios of enantiomers. Sullivan, G. R., in "Topics in Stereochemistry," Eliel et al. eds., Wiley-Interscience, New York (1978), page 263. This method is successful due to the fact that solution diastereomers are formed by the interaction of the chiral shift reagent with some functional group of the enantiomers (e.g., a ketone functional group). The procedure is excellent because it is direct, no chemical modification is necessary, and it is relatively inexpensive. On the other hand, applicability of the procedure is limited because it requires the chiral center in question to be proximal (usually one or two atoms removed) to the chiral shift reagent, thus forming contact diastereomers. If the chiral center is distant to the shift reagent then this method fails. In addition, use of high concentrations of these shift reagents causes line broadening in the NMR spectrum which makes interpretation difficult.

In another approach, chiral solvent has been used for the NMR determination of enantiomeric ratios. Again, this is a trial and error method and the cost of these solvents can be prohibitive.

Ratios of enantiomers in some compounds can be evaluated after the preparation of diastereomeric derivatives, such as Mosher's acid ($\alpha$-methoxy-$\alpha$-trifluoromethylphenylacetic acid) and their subsequent evaluation by NMR spectroscopy. Dale et al., J. Amer. Chem. Soc. 95:512 (1973); Williams et al., J. Amer. Chem. Soc., 110:1547 (1988); Vandewalles et al., Tetrahedron 42: 4035 (1986). Enanatiomeric ratios of secondary alcohols and amines usually can be obtained from the $^{19}$F NMR of their corresponding Mosher's ester derivatives (structure I).

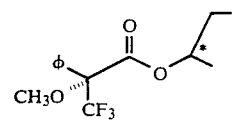

This method relies on the fact that the ester derivatives are diastereomeric and the $^{19}$F nucleus has adequate sensitivity to detect their physical differences. Note, however, that the fluorine nucleus can be no closer than, nor further than five bonds removed from the Mosher's ester chiral center. In fact, even at five bonds sometimes resolution of the resonances is not great enough for quantitative measurements. Another drawback of this method is the cost of Mosher's acid (1 gram cost $30–$40), even though the acid is recoverable via hydrolysis.

In a related approach, Johnson has recently reported the use of $^{31}$P NMR spectroscopy in the determination of enantiomeric purities of alcohols and amines via the use of the oxazaphospholidine-2-sulfide (commercially available from Fluka). Johnson et al., J. Amer. Chem. Soc. 106:5019 (1984) However, several limitations exist with this method. For example, this method is only useful for secondary alcohols and amines. The recycle time is reported to be 60 seconds, which for "normal" concentrations requires prohibitively long NMR experiment times. The sensitivity is marginal as manifested in the reported $\Delta\delta$ (0.100–0.350 ppm).

Both Mosher's acid and oxazaphospholidine-2-sulfide possess the same drawback; only secondary alcohols and amines can be evaluated with these reagents which severely limits these detection methods.

Finally, Trost et al. has reported on the use of O-methyl-mandelate esters to determine enantiomeric excesses at chiral centers by $^1$H NMR spectroscopy quantitation of the methoxy resonances. This method has the added advantage of assigning the absolute configuration of the chiral center, in most cases, by comparison of the chemical shifts as to whether the major methoxy $^1$H resonance is deshielded or shielded. An added bonus is that this method uses routine $^1$H NMR spectroscopy in which every student involved in total synthesis and the development of new synthetic methods or organic chemistry becomes proficient. Again, however, only secondary alcohols and amines can be evaluated, which severely limits this detection method.

It is an object of the present invention to provide an approach to evaluation of enantiomeric ratios which is comparatively easy to use and provides superior versatility in the type of compounds which can be evaluated.

It is a further object of the invention to provide an approach to evaluation of enantiomeric ratios which has high sensitivity.

SUMMARY OF THE INVENTION

In accordance with the present invention, selenium reagents when coupled to a compound containing an asymmetric carbon atom can be used in a highly sensitive method for determination of enantiomeric purity and for stereochemical assignment. Preferred reagents include a selenocarbonyl moiety (Se=C) and a receive center for coupling to the compound of interest. Since the ability of the reagent to resolve enantiomers decreases as the number of bonds between the selenium and the asymmetric carbon increases, this reactive center is preferably located no more than three bonds from the selenium atom.

Particularly preferred selenocarbonyls for use in the invention are selenooxazolidinones of the formula

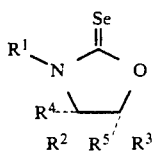

wherein $R^2$, $R^3$, $R^4$ and $R^5$ are selected from among hydrogen, alkyl of up to 10 carbons and aryl having up to 12 carbon atoms in the ring system. The substituent $R^1$ is selected to facilitate the formation of a bond between the nitrogen atom of the selenooxazolidinone reagent and the compound of interest. For example, when the compound of interest is a carboxylic acid or can be converted to a carboxylic acid without disturbing the configuration of the asymmetric carbon atom, $R^1$ is advantageously hydrogen. This permits the formation of an amide linkage between the carboxyl group of the compound of interest and the nitrogen atom of the selenooxazolidinone.

DETAILED DESCRIPTION OF THE INVENTION

Figure 1A:
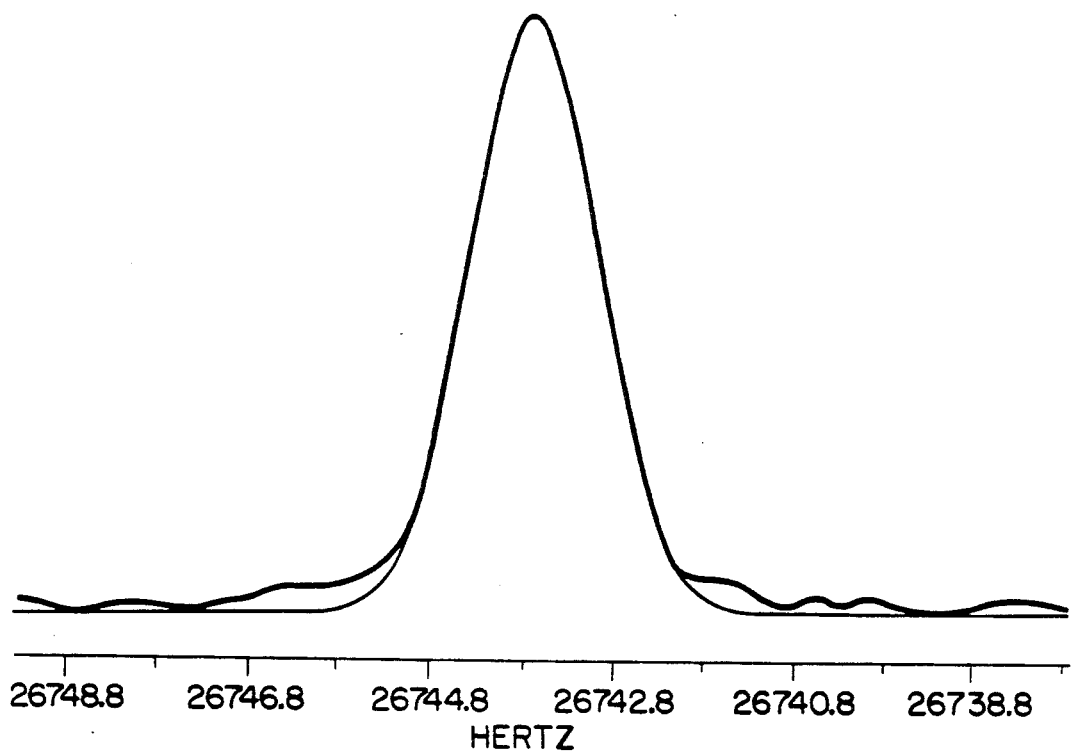

The present invention provides a method and reagents for determining enantiomeric purity and for making stereo chemical assignments of a chemical compound of interest having at least one chiral carbon atom and a reactive center. As used herein, the term reactive center refers to a group within the molecule such as a carboxylic acid, halide, alcohol or amine which can react with a part of a selenium chiral auxiliary reagent. This reaction can occur with the selenium atom, or with another part of the auxiliary reagent.

The remainder of the compound of interest is referred to herein as a substituted or unsubstituted hydrocarbon. This phrase includes straight and branched chain hydrocarbons (saturated and unsaturated), cyclic hydrocarbons, arenes, and linear cyclic compounds incorporating heteroatoms such as O or N.

A. Preparation and Coupling of Selenocarbonyl Reagents

Selenooxazolidinone compounds can be formed, by a method which is part of the invention, starting with a chiral salt of the general formula

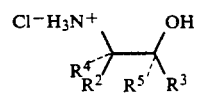

For example, selenooxazolidinones in which $R^2$ is methyl and $R^3$ is phenyl and $R^4$ and $R^5$ are hydrogen can be synthesized from chiral norephedrine hydrochloride. Heiner et al., Angew. Chem. Int. Ed. Engl. 26:894 (1987). This compound, shown as structure 2 in reaction scheme I, is first converted to an amino alcohol in a free-basing step with a base such as 2N sodium hydroxide. The resulting amino alcohol is then reacted with a suitable protective group for the hydroxyl group. This can be accomplished using 1.0 equivalent of NaH and tert-butyl-dimethylsilyl chloride (TBS) in tetrahydrofuran (THF). Conversion of the protected compound to the formamide is effected with formic acid, followed by azeotropic removal of water to give compound 3 in scheme I.

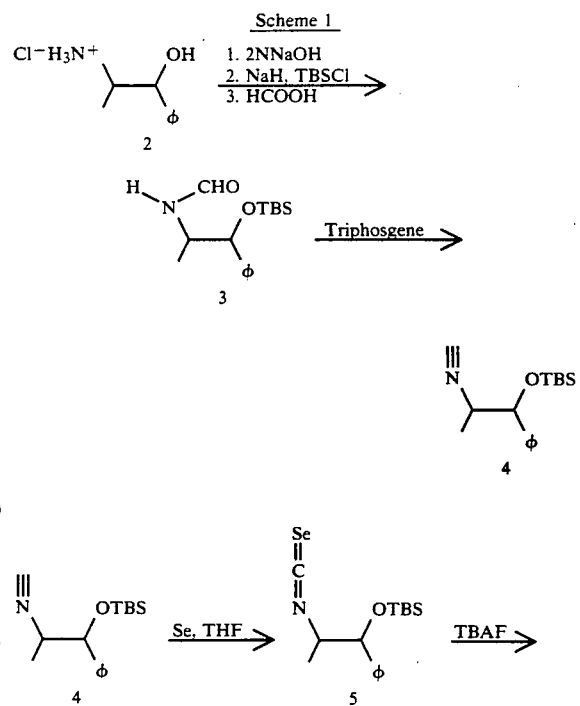

-continued
Scheme 1

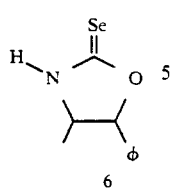
6

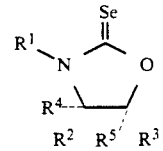

in high yield (80–95% for each step). This compound can be coupled to carboxylic acid compounds by formation of an amide linkage. Further modification of this compound provides compounds which are useful in evaluation of alcohols and amines.

The formamide (3) is next converted to the corresponding isocyanate (4). This can be accomplished using 0.33 equivalents of triphosgene in methylene chloride and triethylamine at room temperature.

The next step in the synthetic method of the invention is the introduction of selenium into the compound. To this end, reaction of the isocyanate (4) with elemental selenium in refluxing THF converts the isocyanate to the isoselenocyanate (5) in good yields. The product can be confirmed by $^{77}$Se-NMR and has a chemical shift of $-346$ ppm using $(CH_3)_2Se$ in $CDCl_3$ as a reference.

The final step of the reaction sequence involves closure of the ring by formation of a bond between the oxygen atom and the carbon atom of the isoselenocyanate moiety. This is formally the addition of an alcohol to the selenocyanate to form a selenocarbamate. Reports of previous efforts to carry out such a reaction have taught that this reaction is sluggish and that the product selenocarbamate is unstable. We have found, however, that this instability was due to extreme reaction conditions rather than an inherent instability of the product. The use of less rigorous conditions, for example tetrabutylammonium fluoride (TBAF) in THF at 0° C. which both cleaves off the protective group and activates the alcohol, results in a stable product in high yield.

The synthetic method set forth in reaction scheme I provides the product compound For example, compound 6 can be converted to a carbamyl chloride by reaction with phosgene or a phosgene equivalent, such as triphogene, in the presence of dimethylaminophridine (DMAP). (Scheme III) The carbamyl chloride (38) should react readily on warming with alcohols or amines to form carbamate or urea products (40). Compound 6 might also be converted to the carbamic acid (39) by reaction with BOC-ON followed by trifluoroacetic acid (TFA).

Alkyl halides, particularly primary alkyl halides should also react facily with compound 6 via either of the pathways shown in Scheme III. Thus, compound 6 or its derivatives provide a single basic reagent which can be used to evaluate four major classes of substituted hydrocarbons, i.e., alcohols, carboxylic acids, amines and halides. In the case of other classes of compounds, modification of an existing active center to one of those noted above, will further broaden the useful scope of the invention.

Other selenocarbonyl compounds can also be used to provide information concerning the stereochemistry of substituted hydrocarbon species. For example, scheme IV shows the synthesis of a isoselenocyanate reagent (36) from a chiral 1-phenylethylamine (35) via formamide, and isocyanate intermediates. Compound (36) will react directly with amines at room temperature in THF to produce compound (37), wherein R is the amine residue. Addition of alcohols to this compound can be accomplished using the corresponding

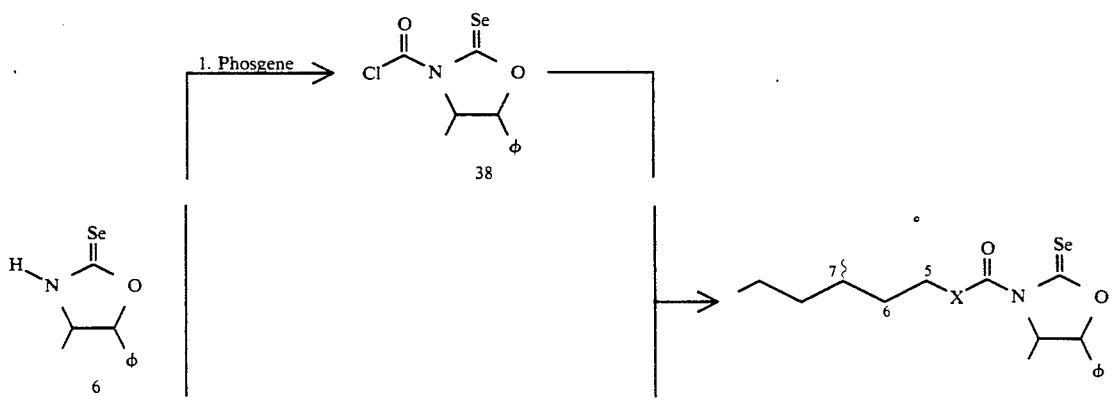

Scheme 2

-continued
Scheme 2

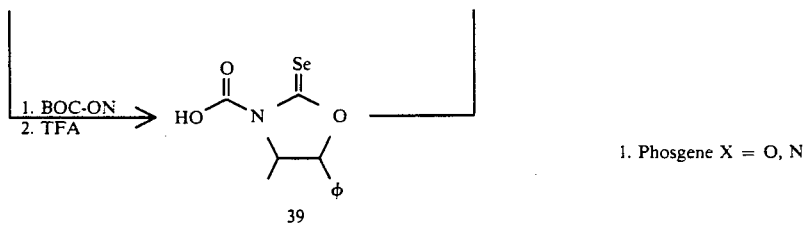

1. Phosgene X = O, N

Scheme 3

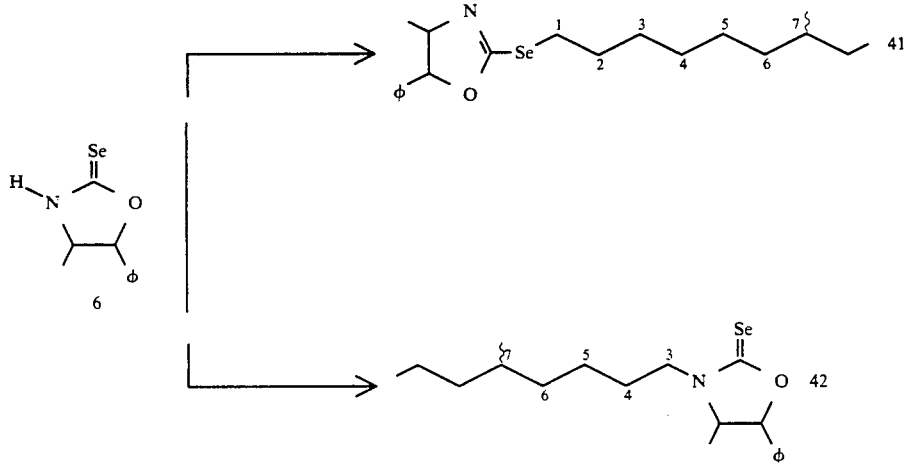

Scheme 4

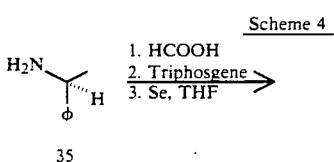

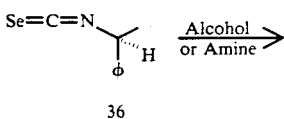

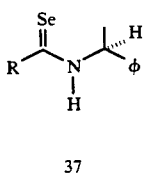

trimethyl-silyl derivative. Just as is the case for cyclization of compound 6, cleavage of the silyl group with TBAF should catalyze the addition of the alcohol to the isoselenocyanate.

In addition to the foregoing type of coupling schemes in which the asymmetric compound of interest is coupled via a nitrogen atom in the selenium reagent, it is also possible to the Se having coupling directly to the Se atom. This is advantageous in that the selenium atom is now closer to the asymmetric carbon atom. On the other hand, there is a loss of sensitivity because the selenium is no longer present as a selenocarbonyl.

B. $^{77}$Se-NMR Analysis

Selenium-77 NMR has been evaluated to determine fundamental magnetic resonance parameters of selenium (i.e. relaxation times, chemical shifts and coupling constants), Luthra et al. in "The Chemistry of Organic Selenium and Tellurium Compounds Vol. 1." Patai et al. eds., John Wiley & Sons (1986), and for NMR studies of selenium-containing proteins. Selenium-77 NMR is very attractive for biochemical studies because of the special features germane to this nucleus and attention has focused mainly on using this nucleus to probe various enzymes, providing intimate knowledge about the enzyme binding pocket and providing information on the mechanism of action. In addition, various kinetic and physical constants can be determined.

The properties of the Selenium-77 nucleus render it highly suitable for use in determining enantiomeric ratios. For Selenium-77, sensitivity is adequate ($6.93 \times 10^{-3}$ with respect to $^1$H and 2.98 compared to $^{13}$C) and its natural abundance (7.5%) and spin ($I = \frac{1}{2}$) are compatible. Parallels have been drawn between $^{77}$Se and $^{31}$P chemical shifts with the sensitivity of the selenium shielding to changes of electronic structure being several times greater. Selenium has the special feature of possessing a large chemical shift range ($\sim 3000$ ppm) and it is extremely sensitive to its electronic environment. In fact, selenium NMR spectroscopy has been shown to be sensitive to centers up to seven bonds removed. (See infra and Rabenstein et al., J. Mag. Res. 1079 (1988).) Thus, the present inventors concluded that very remote chiral centers can be distinguished and thus, the determination of enantiomeric purity can be accomplished using $^{77}$Se NMR.

In designing the selenium chiral auxiliaries of the invention, advantage was taken of the fact that the chemical shifts of selenocarbonyl groups are spread over a large chemical shift range. The $^{77}$Se chemical shift of COSe is most shielded at −447 ppm and the Se resonance in (t-Bu)$_2$CSe is the most deshielded at 2131 ppm. In fact, the chemical shifts of compounds containing the C=Se moiety appear as a class to have a larger chemical shift range than any other type of Se compound. In addition, the T$_1$'s of the C=Se compounds are relatively short (~8 s) while the dialkyl selenides and especially the diaryl and dibenzyl selenides are fairly long (27.0 s). Clearly, long T$_1$'s would reduce the feasibility of using selenium NMR spectroscopy in the determination of enantiomeric excesses at remotely disposed chiral centers by making the time necessary to perform the NMR experiment prohibitively long. More importantly, selenocarbonyl groups display a remarkable sensitivity (as compared to diselenides) toward small changes in the electronic structure of the Se atom and its directly bonded carbon atom. This sensitivity is manifested in an astounding chemical shift range for C=Se moiety of more than 2600 ppm ' The known chemical shift range for all Se compounds is on the order of 3000 ppm. Thus, the range for C=Se approaches the current limits of the $^{77}$Se NMR chemical shift range.

C. Evaluation of Enantiomeric Excesses

The benefits of this sensitivity are evident when one considers the observed results of coupling compound 6 to a variety of racemic carboxylic acids which contain methyl groups that are sequentially one carbon removed from the carbonyl carbon (Scheme V). The coupling method of choice involves the use of dicyclohexylcarbodimide (DCC) in CH$_2$Cl$_2$ with DMAP at 0° C., for 0.5–1.0 hrs. Filtration through a pad of silica gel and solvent removal followed by purification (silica gel flash chromatography) yields the acylated 6 in 90–95% yields. A $^{77}$Se-$^{13}$C coupling constant of ~230 Hz in compound 8 indicates N-acylation, which is in accordance with literature values for selenocarbonyl derivatives. Cullen et al., J.C.S. Perkin Trans. I; 473 (1982). We are aware of the possibility of the coupling of the selenium-end of the ambident anion with the activated acid to give the corresponding selenoester derivatives and would anticipate useful results of this were formed. However, $^{13}$C NMR, $^{77}$Se NMR, and the $^{77}$Se-$^{13}$C coupling constant support our identification of the compound as the N-acylated adduct.

Figure 1B:
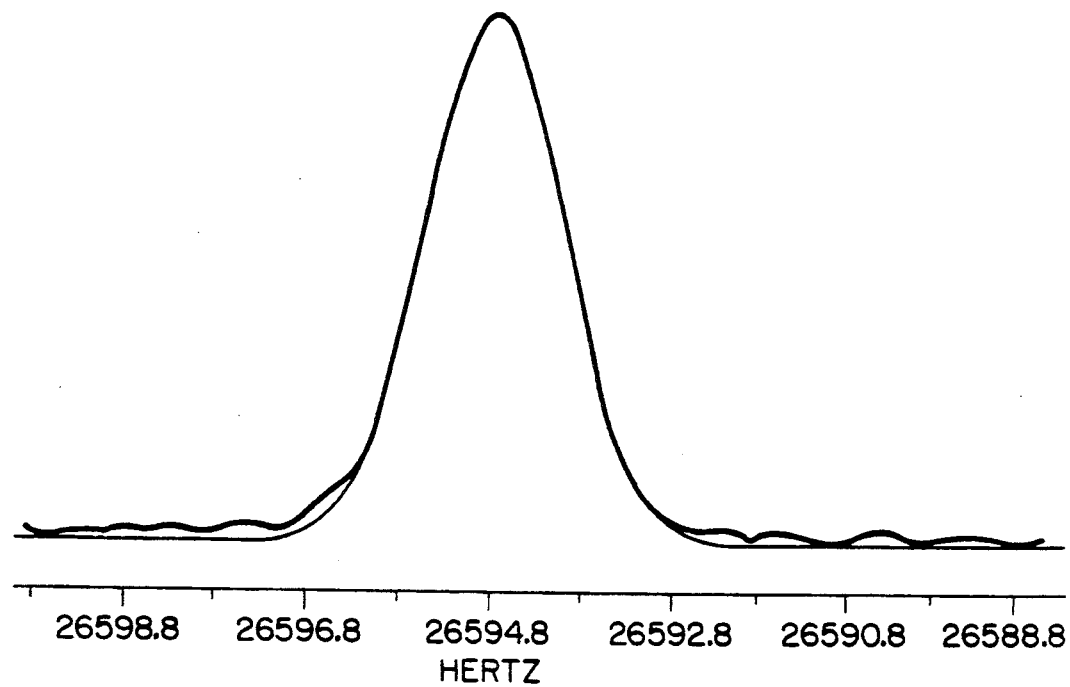

Scheme V illustrates a series of acylated selenoox-azolidinone which have been evaluated by $^{77}$Se NMR, spectroscopy. The selenium-77 NMR spectra illustrated in FIGS. 1A and 1B were obtained in the Fourier transform mode on a AM Bruker-300 superconducting spectrometer at 7.05 Tesla. Chemical shifts were measured with respect to a 60% (CH$_3$)$_2$Se in CDCl$_3$. Positive chemical shifts denote resonances that are deshielded with respect to the reference. Measurements were typically made at, or near, ambient probe temperature in 5-mm NMR tubes using CDCl$_3$ as an internal lock solvent. All spectra were acquired in the proton-decoupled mode; generally, 0.15–0.30M solutions were used and 128–1024 scans were acquired using a pulse angle of 30° and a recycle time of 2.2 s. A resolution of 0.1 ppm was obtained using an 32K data table and a sweep width of 100 ppm.

Table 1 sets out the chemical shifts of the peaks observed for each of the four carboxylic acids tested, and for mono-deuterated phenylacetic acid. The results illustrate the astounding ability of the invention to resolve different enantiomers when the asymmetric carbon is 7 bonds removed from the selenium atom.

TABLE 1

| Compound | Chemical Shifts of Enantiomers | Differences in Chemical Shift |
|---|---|---|
| 8 | 449.35 | 3.1 ppm |
|   | 452.45 |  |
| 10 | 464.6 | 2.6 ppm |
|    | 467.2 |  |
| 12 | 467.1 | 0.4 ppm |
|    | 467.5 |  |
| 14 | 466.65 | 0.094 ppm |
|    | 466.75 |  |
| 16 | 471.045 | 4.0 Hz |
|    | 471.116 |  |

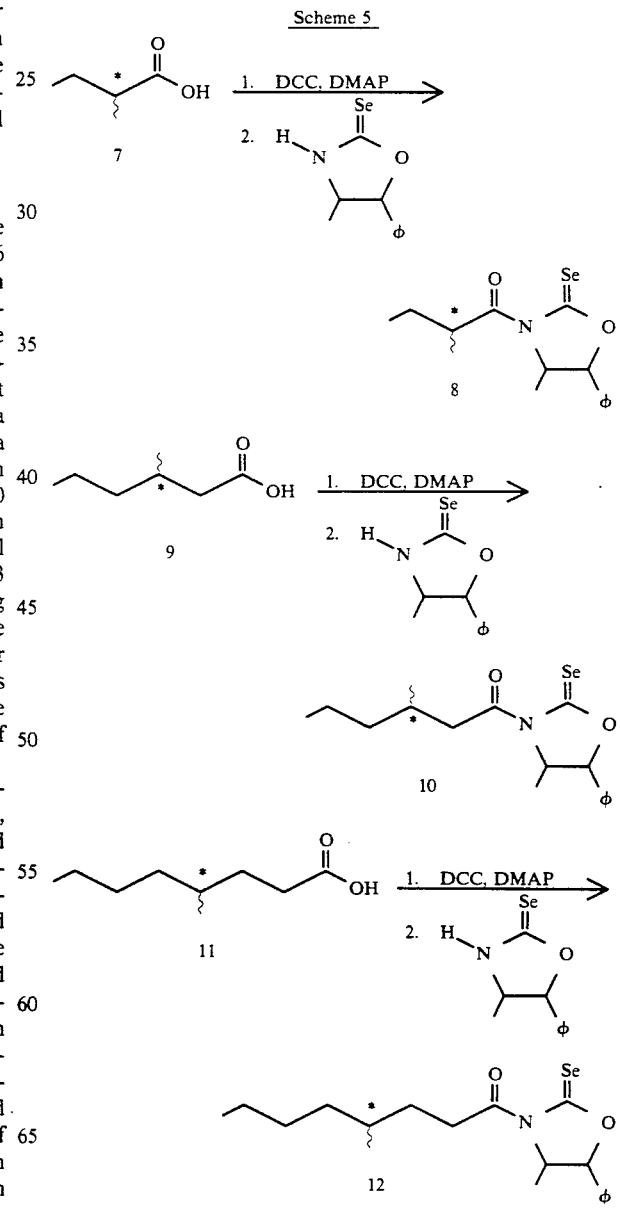

Scheme 5

-continued
Scheme 5

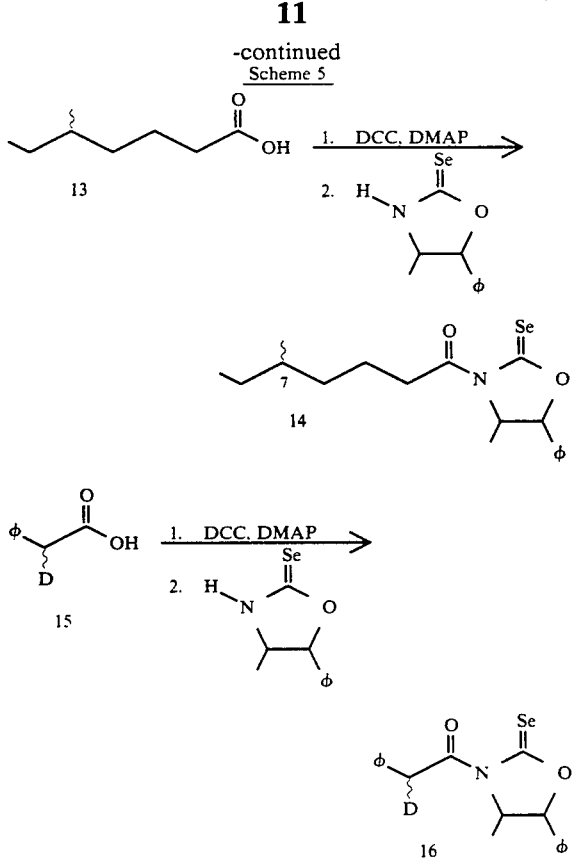

A further dramatic example of the sensitivity of selenium NMR spectroscopy is provided by the phenylacetic acid derivative 16. This compound exhibited four resonances in its $^{77}$Se NMR spectrum. The largest peak has been assigned to the fully protonated species which has a chemical shift at δ 471.7 ppm. The monodeuterated species are, in principle diasteromeric and are anisochronous, i.e., they have different chemical shifts. These monodeuterated species exhibited observable differences of 4 Hz and have chemical shifts at δ 471.1 and 471.0 ppm. Increased resolution should be possible through better shimming and changing the NMR solvent. In addition, increased digitization and narrowing of the window will increase the resolution. The most shielded peak has been assigned to the bisdeuterated species which resonates at δ 471.4 ppm. Not only is it remarkable that the selenium nucleus has the special ability to distinguish between a hydrogen and a deuterium four bonds removed, but it can also discern the presence of four different species (with a Δδ range of 1.3 ppm) which differ only by the number and nature (diastereotopic) of deuterium atoms present. Clearly, from these results we were readily able to discern that our deuterium incorporation was fortuitously incomplete even though the integration of the parent carboxylic acid was in complete agreement with at least 95% deuterium incorporation.

In order to use Selenium 77 NMR to determine actual enantiomeric ratios rather than simply to identify the presence or absence of particular species, it is necessary to make quantitative intensity measurements (integration) of $^{77}$Se spectra. Based on preliminary experiments performed at 7.05T ($^{77}$Se at 57.24 MHz) using compound 10 to evaluate the accuracy with which measurements can be made under rigidly quantitative conditions and the sensitivity of measurements to carefully controlled deviations from quantitative conditions, we conclude that quantitative measurements are feasible.

Quantitative measurements of NMR peak areas require careful attention to relaxation rates and to phenomena such as the nuclear Overhauser effect (nOe) which may lead to distortions in apparent areas. If one is to measure the area of two peaks derived from a pulse/Fourier transform NMR experiment, the degree of spin-lattice relaxation between successive pulses must be the same for both resonances. This will be rigidly true for all possible pulse intervals only if the $T_1$ relaxation rate is the same for both resonances. Where $T_1$ is unequal, a repetition rate must be chosen such that the time between measuring pulses is very much longer than the longer of the two $T_1$ relaxation times. Similarly, if two resonances exhibit different enhancement factors attributable to nOe's, the nOe's must be suppressed. Suppression of nOe's which arise during broadband $^1$H decoupling are a result of internuclear dipolar relaxation and may be suppressed by a suitable decoupler gating scheme provided the interval during which the $^1$H's are not irradiated is at least 9 to 10 times the $^{77}$Se $T_1$ relaxation time. Cannet, D., J. Magn. Reson. 23:361 (1976); Harris et al., J. Magn. Reson. 24:449 (1976).

In order to measure the areas of the two resonances of interest under rigorously quantitative conditions, an upper limit on $T_1$ was determined from the optimum top angle, a, using the equation of Ernst and Anderson $$\cos(a) = \exp(-t/T_1)$$

where t is the pulse spacing. Rev. Sci. Instrum., 37:93 (1966). $T_1$ was found to be less than 9 seconds for both resonances and spectra were acquired with and without nOe suppression with relaxation delays of 93 seconds. Acquisition times were chosen to be longer than 5 times $T_2$, insuring accurate determination of peak line shapes and data were zero-filled to improve digital representation of the line shape. Line integrals customarily used in NMR spectroscopy are rarely accurate to more than 5%. Errors arise due to inclusion of incomplete averaged noise within the integral boundaries and from subjective attempts to minimize contributions due to non-zero baselines (so called drift and bias corrections). Weiss and Ferritti have analyzed the problems of accurately measuring integrals in the context of measuring nOe's. J. Magn. Reson. 55:397 (1971). We feel more accurate and reproducible integrals may be derived by first curve fitting the data in an objective manner and subsequently calculating the integrals from the parameters of the best fit curves (for a representative sample see FIG. 1). For all our area measurements, a mild gaussian weighting function (GB=0.1) was applied to the FID prior to Fourier transformation. The resulting frequency domain spectra had an rms (root mean square) signal to noise ratio of ca. 60:1. Using curve fitting routines in Bruker's DISNMR program, each resonance was fit by a gaussian line shape. Iteration was performed automatically until the convergence limit of $1 \times 10^{-8}$ was achieved (5 to 9 iterations depending on the quality of the data). Residual standard deviations were on the order of 0.1 to 0.3. We feel that integrals determined in this manner may be precise to better than +/−0.5% provided careful attention is paid to signal to noise ratios and proper digitization of data. By comparison, it is suggested by Derome that an rms signal to noise of better than 250:1 is required to reduce the uncertainty in the measurement of traditional line integrals to +/−1T of the true value.

D. Assignment of Stereochemical Configuration

As is clear from the assignments made for the monodeuterated compound 16, assignments of absolute stereochemical configuration can be made based upon the observed chemical shifts. This is done by determining from molecular models the relative shielding existing in the two enantiomers and thus which of the enantiomers will have the greatest chemical shift. This same approach can be readily employed to assign absolute configuration to other stereochemical pairs.

What is claimed is:

1. A method of determining enantiomeric purity for a compound having an asymmetric carbon and a reactive center comprising the steps of
   (a) coupling the compound via the reactive center with a reagent containing a selenium atom such that the selenium atom is within 7 bonds of the asymmetric carbon atom;
   (b) observing the frequencies and intensities of radio frequency absorption peaks of the $^{77}$Se atoms by $^{77}$Se-nuclear magnetic resonance spectroscopy; and
   (c) comparing the intensities of the observed peaks to determine the amount of enantiomeric excess, wherein the reagent is a chiral reagent having the formula

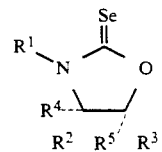

wherein $R^1$ is H,

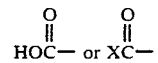

and X is halogen, and
$R^2$, $R^3$, $R^4$ and $R^5$ which may be the same or different are selected from hydrogen, alkyl of up to 10 carbon atoms and aryl having up to 12 carbon atoms in the ring system.

2. A method according to claim 1, wherein $R^1$ is H and the compound is a carboxylic acid.

3. A method according to claim 2, wherein $R^2$ is methyl, $R^3$ is phenyl, and $R^4$ and $R^5$ are hydrogen.

4. A method according to claim 1, wherein the coupling step is carried out in a mixture comprising dicyclohexylcarbodimide and dimethylaminopyridine.

5. A method according to claim 1, wherein the absorption peaks are observed by making successive individual observations using a Fourier transform spectrometer.

6. A method according to claim 5, wherein the successive individual observations are separated by a time interval of sufficient length to allow substantially complete relaxation of both enantiomeric species.

7. A method according to claim 6, wherein the absorption peaks are observed in proton decoupled mode.

* * * * *

UNITED STATES PATENT AND TRADEMARK OFFICE
CERTIFICATE OF CORRECTION

PATENT NO. : 5,122,472

DATED : June 16, 1992

INVENTOR(S) : Silks III, et al.

It is certified that error appears in the above-identified patent and that said Letters Patent is hereby corrected as shown below:

Abstract, line 10,
"                                         "

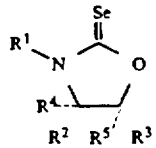     should read --     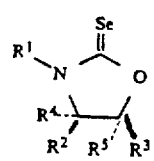     --;

Col. 3, line 31, "receive" should read -- reactive --;

Col. 3, line 40,
"                                         "

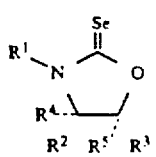     should read --     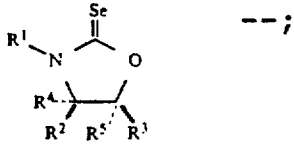     --;

Col. 6, line 1,
"                                         "

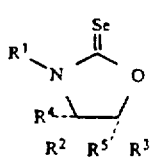     should read --     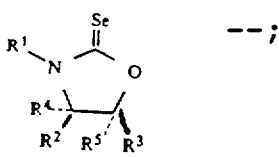     --;

UNITED STATES PATENT AND TRADEMARK OFFICE
CERTIFICATE OF CORRECTION

PATENT NO. : 5,122,472

DATED : June 16, 1992

INVENTOR(S) : Silks III, et al.

It is certified that error appears in the above-identified patent and that said Letters Patent is hereby corrected as shown below:

Col. 8, line 1, "1. Phosgene X = O,N" should read --X = O,N--;

Col. 14, line 1,
" 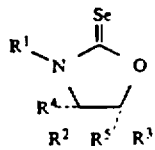   should read --  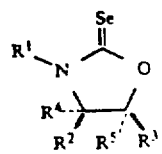  --;

Col. 14, lines 25-26, "dicyclohexylcabodimide" should read --dicyclohexylcarbodiimide--.

Signed and Sealed this

Twenty-fourth Day of August, 1993

Attest:

BRUCE LEHMAN

Attesting Officer

Commissioner of Patents and Trademarks